US006876758B1

(12) United States Patent
Polat et al.

(10) Patent No.: US 6,876,758 B1
(45) Date of Patent: Apr. 5, 2005

(54) METHODS AND SYSTEMS FOR IMPROVING A USER'S VISUAL PERCEPTION OVER A COMMUNICATIONS NETWORK

(75) Inventors: Uri Polat, Gedera (IL); Nir Ellenbogen, Hod Hasharon (IL); Dov Sella, Even Yehuda (IL)

(73) Assignee: Neuro Vision, Inc., Singapore (SG)

( * ) Notice: Subject to any disclaimer, the term of this patent is extended or adjusted under 35 U.S.C. 154(b) by 541 days.

(21) Appl. No.: 09/711,354

(22) Filed: Nov. 9, 2000

Related U.S. Application Data

(63) Continuation-in-part of application No. 09/642,506, filed on Aug. 18, 2000, now abandoned.

(30) Foreign Application Priority Data

Dec. 27, 1999 (IL) .................................................. 133758

(51) Int. Cl.[7] ............................ G06K 9/00; G09G 5/00
(52) U.S. Cl. ....................... 382/128; 382/114; 345/729; 345/865
(58) Field of Search ................................ 382/128, 181, 382/114; 345/744, 866, 729

(56) References Cited

U.S. PATENT DOCUMENTS

| 4,365,873 A | 12/1982 | Ginsburg ................. 351/239 |
| 5,176,147 A | 1/1993 | Bodis-Wollner ............ 128/745 |
| 5,206,671 A | 4/1993 | Eydelman et al. .......... 351/203 |

(Continued)

FOREIGN PATENT DOCUMENTS

| EP | 0 411 821 A1 | 6/1991 |
| EP | 0544 631 A2 | 6/1993 |
| WO | WO 00/77760 A1 | 12/2000 |

OTHER PUBLICATIONS

Uri Polat and Dov Sagi (Israel, 1995) "Plasticity of Spatial Interactions in Early Vision" *Maturational Windows and Adult Cortical Plasticity* pp. 111–125.

Uri Polat and Dov Sagi (Great Britain, 1994) "The Architecture of Perceptual Spatial Interactions" *Vision Research* vol. 34, No. 1, pp. 73–78.

Uri Polat and Dov Sagi (Feb. 1994) "Spatial interactions in human vision: From near to far via experience–dependent cascades of connections" *Proc. Natl. Acad. Sci. USA* vol. 91, pp. 1206–1209.

Dennis M. Levi and Uri Polat (Jun. 1996) "Neural plasticity in adults with amblyopia" *Proc. Natl. Acad. Sci. USA* vol. 93, pp. 6830–6834.

Uri Polat, Dov Sagi, and Anthony M. Norcia (Great Britain, 1997) "Abnormal Long–range Spatial Interactions in Amblyopia" *Vision Research* vol. 37, No. 6, pp. 737–744.

Dennis M. Levi, Uri Polat, and Ying–Sheng Hu (USA, Jul. 1997) "Improvement in Vernier Acuity in Adults With Amblyopia" *Investigative Ophthalmology & Visual Science* vol. 38, No. 8, pp. 1493–1510.

Dennis M. Levi and Vineeta Sharma (Great Britain, 1998) "Rapid Communication, Integration of Local Orientation in Strabismic Amblyopia" *Vision Research* vol. 38, No. 6, pp. 775–781.

Uri Polat (1999) "Functional architecture of long–range perceptual interactions" *Spatial Vision* vol. 12, No. 2, pp. 143–162.

*Primary Examiner*—Leo Boudreau
*Assistant Examiner*—Shefali Patel
(74) *Attorney, Agent, or Firm*—G. E. Ehrlich (1995) Ltd.

(57) ABSTRACT

Methods and apparatus that provide proper identification of visual and neurological abilities related to defects in the neurological component of the brain, that improve visual and neurological performance, and that develop improved neural performance in the brain and nervous system. All of these methods are carried out over a communications network such as the Internet.

22 Claims, 10 Drawing Sheets

U.S. PATENT DOCUMENTS

| | | | |
|---|---|---|---|
| 5,589,897 A | | 12/1996 | Sinclair et al. .............. 351/223 |
| 5,802,530 A | * | 9/1998 | Van Hoff .................... 715/513 |
| 5,868,683 A | * | 2/1999 | Protopapas et al. ......... 600/559 |
| 5,956,121 A | * | 9/1999 | Hosoi et al. ................. 351/205 |
| 5,956,126 A | | 9/1999 | Cody ......................... 351/246 |
| 6,026,433 A | * | 2/2000 | D'Arlach et al. ........... 709/217 |
| 6,260,022 B1 | * | 7/2001 | Brown ........................... 705/2 |
| 6,331,115 B1 | * | 12/2001 | Jenkins et al. .............. 434/169 |
| 6,386,707 B1 | * | 5/2002 | Pellicano .................... 351/246 |
| 6,430,567 B2 | * | 8/2002 | Burridge ..................... 707/102 |
| 6,560,605 B2 | * | 5/2003 | Albers et al. ................. 707/10 |

* cited by examiner

METHODS AND SYSTEMS FOR IMPROVING A USER'S VISUAL PERCEPTION OVER A COMMUNICATIONS NETWORK

CROSS REFERENCES TO RELATED APPLICATIONS

This application is a continuation-in-part of U.S. patent application Ser. No. 09/642,506, filed on Aug. 18, 2000, now abandoned, which claims the benefit of pending Israeli Patent Application Serial No. 133758, filed on Dec. 27, 1999.

BACKGROUND OF THE INVENTION

1. Field of the Invention

The invention relates generally to the field of improving vision, more specifically, to identifying and improving visual perception and acuity abilities, and improving the visual perception process and neural performance of a user, over a communications network.

2. Background Information

Human eyesight is a product of two separate processes that work together to form images for a person to "see". One of these processes, herein referred to as the physical component, concerns the physical structure of the various elements of the eye and how incoming light is manipulated and processed by the eye. Defects in the shape of the cornea, the retinal wall, or the optic nerve can impair or destroy the functionality of a person's eye and thus impair or eliminate the ability to perceive images. Fortunately, defects in the cornea of a person can be corrected through the use of glasses, contacts, or surgery such as laser keratotomy. Likewise, defects in the retina of a person are often repairable by surgery.

The second process involved in allowing humans to see images is herein referred to as the neurological component. This component concerns neural processing in the brain and how the brain analyzes information sent from the eyes to produce an image for that person to see. A person can likewise have a number of defects in this component of the visual process, such as reduced visual acuity, reduced sensitivity for spatial contrast, reduced vernier acuity, spatial distortion, abnormal spatial interactions and impaired contour detection.

The physical component and the neurological component work together to form images that a person sees, or more precisely, that a person perceives. The term "perceives" is preferred because although the physical component may capture certain details, defects in the neurological component may distort and destroy these details, therefore, the image that is "seen" by the person may not be exactly what is captured by the eyes. Consequently, the image that is perceived may differ in detail from the image that is seen by the eyes. Thus, for the sake of preciseness, the overall process of human eyesight is herein referred to as the visual perception process.

Defects in the neurological component of a person's visual perception process cannot be remedied through the use of corrective lenses or surgery, therefore, alternate techniques must be employed to alleviate or correct visual defects to this neurological component.

For example, a common defect in the neurological component of the visual perception process is a condition known as amblyopia. This is a perception defect where the brain incorrectly interprets and processes visual information it receives from the eyes, despite the fact that the physical structure of the eyes may be unimpaired. When addressing amblyopia in children, one approach to correcting defects in the neurological component is to occlude the nonamblyopic, dominant eye and "force" the brain to make greater use of the amblyopic eye. This approach generally strengthens the amblyopic eye and increases its visual acuity. But a significant shortcoming of this approach is that this method is typically only useful in children under the age of nine, and beyond that age the method generally provides insignificant results. Furthermore, occlusion of the non-amblyopic eye is accomplished through the use of an unsightly eye patch, and this often results in social and emotional problems for children. The eye patch frequently causes skin irritation as well.

Amblyopic observers suffer from many or all of the neurological defects mentioned above, such as reduced visual acuity, reduced sensitivity for spatial contrast, reduced vernier acuity, spatial distortion, abnormal spatial interactions and impaired contour detection. Amblyopes may also have abnormally high degrees of intrinsic noise, which may form the basis of their abnormal contrast sensitivity function.

SUMMARY OF THE INVENTION

The invention addresses a need for methods and apparatus that provide proper identification of visual and neurological abilities related to the condition of the neurological component of the brain, such as visual perception abilities. In addition, the invention provides methods and apparatus for improving visual and neurological performance, such as visual perception ability, and developing improved neural performance in the brain and nervous system. Furthermore, all of these methods are carried out over a communications network such as the Internet.

According to one aspect of the invention, a communications network based system for identifying and improving visual and neurological abilities is provided, comprising a client terminal and a host server communicatively coupled to one another, and a host storage device comprising a computer-readable medium communicatively coupled to the host server, wherein the host storage device has stored therein one or more sequences of processor executable instructions for identifying and improving visual and neurological abilities.

According to another aspect of the invention, a method for remotely identifying and improving visual and neurological abilities comprises sending a plurality of parameters from a host terminal to a client terminal, then at the client terminal using the parameters to generate a set of images, presenting the set of images on a display screen, receiving an input from a user based on the user's perception of the set of images, and generating a further set of images based at least in part upon the parameters and based at least in part upon the user input, then generating and sending user performance data from the client terminal to the host terminal, and finally analyzing the user performance data at the host terminal to identify and improve any visual and neurological abilities.

According to a further aspect of the present invention, there is provided a system for improving improving the visual perception ability of a user, comprising:

a client terminal including a display device, an input device, and a client processor;

and a host server including a host storage device, and a host processor communicatively coupled to said client processor;

said host storage device having stored therein a first plurality of parameters of images selectable to test the visual perception ability of the person with respect to at least one visual defect and to elicit responses from the person indicative of the presence or absence of said at least one visual defect, and a second plurality of parameters of images designed to treat the person with respect to a detected visual defect and thereby to improve the visual perception ability of the person with respect to such detected visual defect;

said display device being controlled by said client processor and host processor for displaying to the person, selected images of said first plurality of parameters and of said second plurality of parameters;

said client processor and host processor being controlled by said client input device:

(a) to receive said first plurality of parameters, to generate a first plurality of images corresponding thereto, and to display said first plurality of images in said display device;

(b) to register the responses inputted by the user via said input device;

(c) to utilize said user responses to select the parameters of said second plurality of images in said host storage device corresponding to the images designed to treat the person with respect to a visual defect detected from said responses; and (d) to control said display device to display to the user, in a treatment phase, the selected images in said second plurality in at least one treatment session until the visual perception ability of the person has been improved with respect to said detected visual defect.

According to yet another aspect of the present invention, there is provided a method of improving the visual perception ability of a person, comprising:

in a client terminal, displaying to the person, in at least one evaluation session of an evaluation phase, a plurality of images selected to test the visual perception ability of the person with respect to at least one visual defect, and to elicit responses from the person indicative of the level of the person's visual perception ability with respect to said at least one visual defect;

communicating the responses of the person to a remotely-located host server;

utilizing said responses to select in the host server another plurality of images designed to treat the person with respect to a detected visual defect and thereby to improve the visual perception ability of the person with respect to the detected visual defect;

and in the client terminal, displaying to the person, in a treatment phase, said another plurality of images in at least one treatment session until the visual perception ability of the person has been improved with respect to said detected visual defect.

DETAILED DESCRIPTION OF THE PREFERRED EMBODIMENTS

1. Terminology

As used herein, the term "Visual Perception Task image" or "VPT Image" refers to an image generated by the invention for use in testing, treating, or improving a user's visual perception process.

As used herein, the term "Visual Perception Task" or "VPT" refers to one or more VPT images that are used alone or in combination with each other to test or improve a user's visual perception process.

As used herein, the term "Visual Perception Task Session" or "VPT Session" refers to a plurality of VPTs that are presented to a user to test or improve their visual perception process. Each VPT Session is generally designed to target a specific aspect of the visual perception process.

2. Visual Perception Task Images

Figure 1:
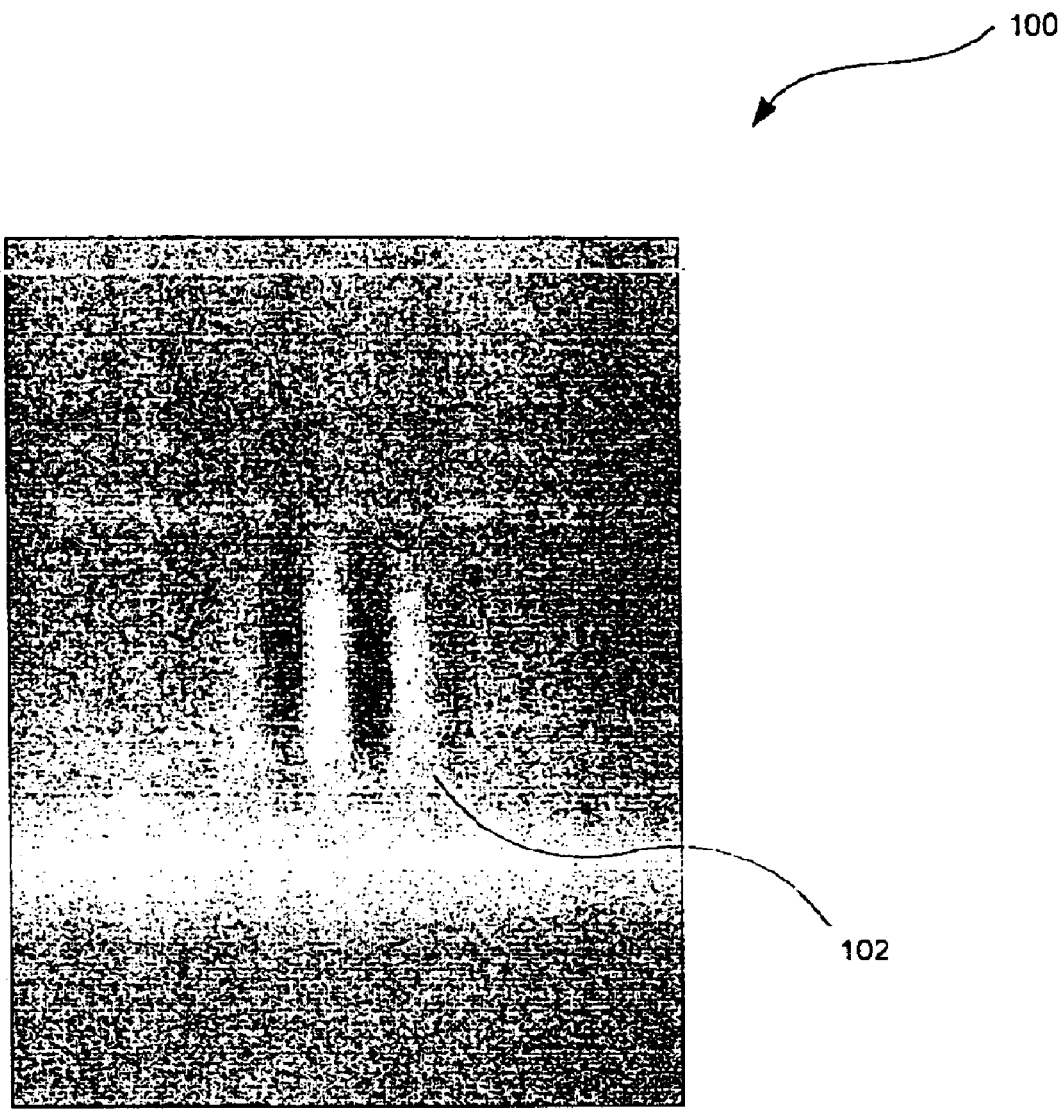
FIG. 1 illustrates one embodiment of a visual perception task image.

Beginning with FIG. 1, an embodiment of a Visual Perception Task Image (VPT Image) of the invention is shown. The VPT Image 100 of FIG. 1 comprises a single target Gabor patch 102 designed to activate neurons in the visual cortex. It should be noted that the VPT Image 100 can take the form of any visual stimulus, and is not limited to Gabor patches.

The Gabor patch 102 is a luminance pattern defined by a collection of odd (sine) and even (cosine) wave functions with limited spatial extent (and/or temporal extent). These functions are referred to as Gabor functions. The Gabor functions include variables that describe the pattern orientation, wavelength (width of a single black-white cycle) and spread of the Gaussian envelope.

Gabor functions are significant because they have been shown to efficiently describe the shape of receptive fields in the mammalian visual system. Neurons in the primary visual cortex receive retinal inputs with weights distributed over space in a shape that fits the Gabor function. In humans, it has been shown that visual pattern detection is performed by multiple localized filters, each covering a range of retinal space, orientations and wavelengths. The filters weigh visual input by a function that fits the Gabor function, each filter having its own parameter set (location, orientation, wavelength). These detectors underlie both pattern detection and segmentation.

Figure 2:
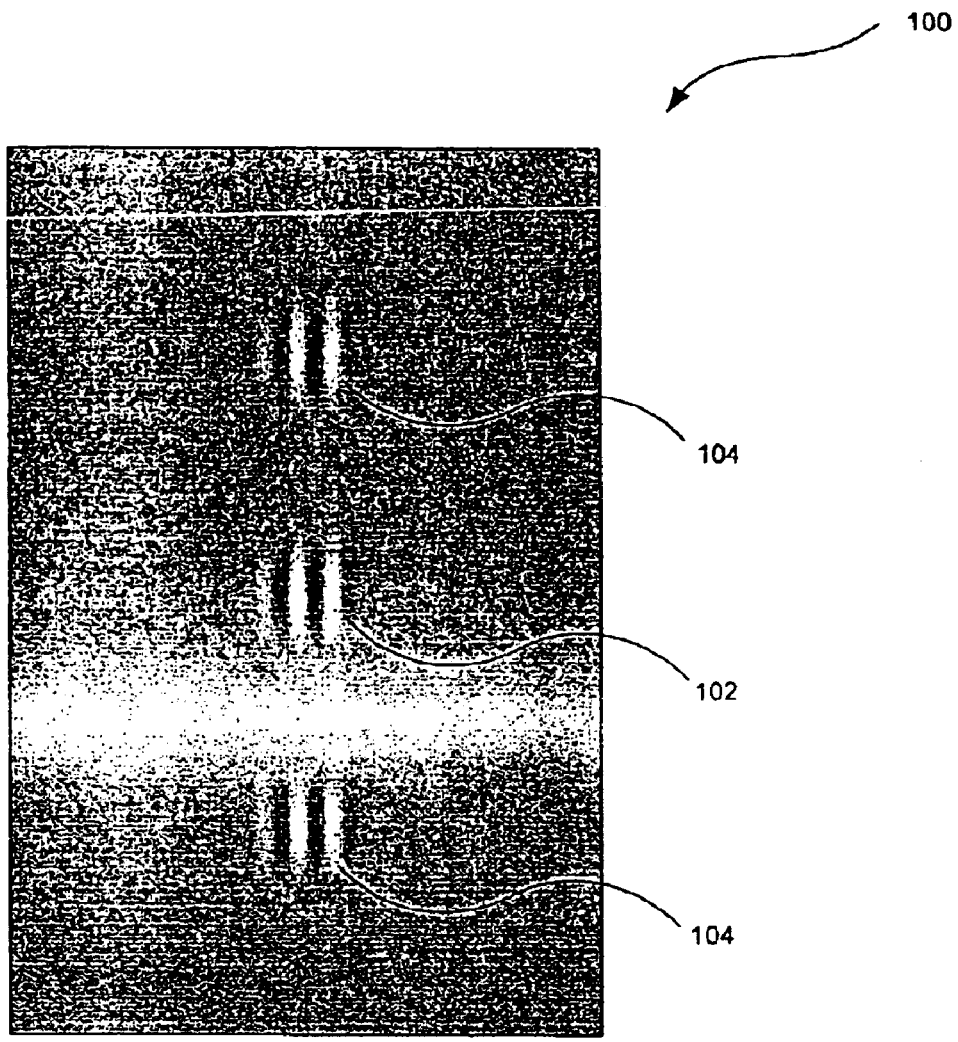
FIG. 2 illustrates a second embodiment of a visual perception task image.

Another VPT Image 100 is illustrated in FIG. 2, this time comprising a central target Gabor patch 102 flanked by two more Gabor patches 104 of similar orientation and spatial frequency placed laterally of the central Gabor patch. In this embodiment, the target Gabor patch 102 preferably coincides with a fixation point of an observer (the target patch 102 being fovean) sitting a distance of about 0.5–2.5 meters from a display screen presenting the VPT image. The Gaussian envelope size ($\sigma=\lambda=0.15°$) may be such that at least one cycle is within a range of $\pm\sigma$ from the Gaussian center. The carrier spatial frequency of the Gabor patches may be 6.6 cycles per degree ($\lambda=0.15°$) and mask contrast may be 40%. The distance d between the target Gabor patch 102 and the flanking patches 104 may be 1.5λ. The initial contrasts of the patches may be in the range of 8–50%, for example. In short, each visual image is characterized by a parameter comprising at least one of a contrast, a spatial frequency, a distance between the images, a local and global orientation, presentation time, and possibly other parameters as well.

It should be noted that the invention comprises a number of alternative embodiments of the VPT Images 100. This is because many visual perception deficiencies exist, and each deficiency generally requires a different set of VPT Images 100 to address and improve it. Therefore, the invention employs a large number of different VPT Images 100 to improve many different types of visual perception deficiencies. These different VPT Images 100 use changes in parameters such as contrast, contours, spatial frequency, distance between the images, local and/or global orientations of the images, and other attributes to develop improved neurological function. Because the VPT Images 100 are typically computer-generated images, they may also be either static or dynamic.

Furthermore, the VPT Images 100 are not restricted to Gabor patches, but rather any kind of visual image, including straight lines, curved lines, or other shapes. The particular VPT Image 100 used is selected based upon which neurological functions require improvement. Accordingly, the embodiments shown in FIGS. 1 and 2 are for purposes of illustration only, and are not meant as limitations on the invention.

Figure 3:
FIG. 3 illustrates further embodiments of the visual perception task image of FIG. 2.

Variations of the VPT Images of FIGS. 1 and 2 not shown are also used by the invention. For example, another variation of the VPT Image 100 of FIG. 1 may consist of sequentially adding one or more flanking Gabor patches 104 that are similar in appearance to the target Gabor patch 102. And for the VPT Image 100 of FIG. 2, a variation may consist of rotating the local orientations of the Gabor patches 102 and 104, as well as their global orientation. These alternate variations of the VPT Image 100 of FIG. 2 are shown in FIG. 3.

3. Visual Perception Tasks

A Visual Perception Task (VPT) comprises one or more VPT Images 100 that are presented to a user in sequence, wherein at least one of the VPT Images 100 generally includes a target. As used herein, the term "target" refers to a specific image that the user is expected to focus on or detect, such as a Gabor patch or some other visual stimulus. When two or more VPT Images 100 are used in a VPT, generally less than all of the VPT Images 100 used will contain the target. For example, if two VPT Images are used, one VPT Image will have the target while the other VPT Image will not. The VPTs vary, thus there may be a single static or dynamic VPT Image used in a VPT, or there may be two or more VPT Images displayed in sequence.

Figure 4A:
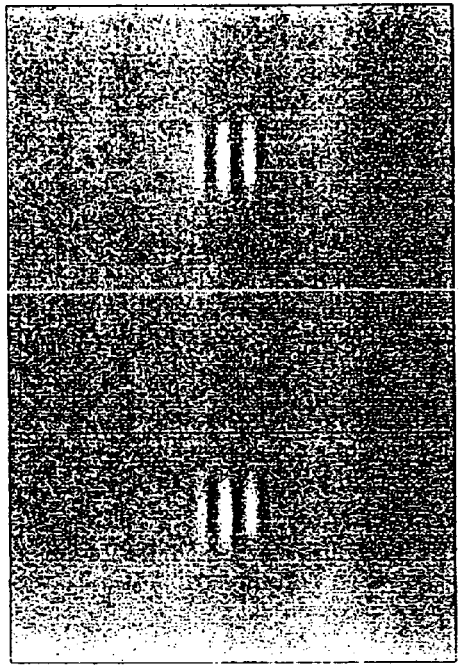
FIGS. 4A and 4B illustrate one embodiment of a visual perception task.
Figure 4B:
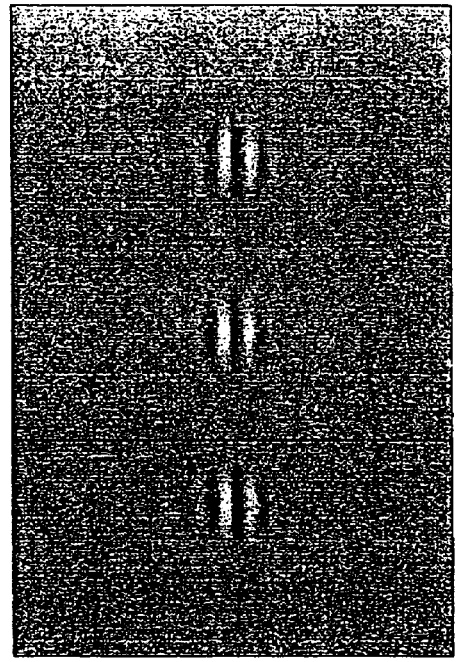

Turning to FIGS. 4A and 4B, an example of a VPT is shown. In this example, the VPT uses two VPT Images 100. The VPT begins with a user focusing on a target area, which is generally the center of the display screen. Some form of marker may be displayed prior to the VPT Images 100 being shown to aid the user in focusing on the target area. Next, the two VPT Images 100, shown in FIGS. 4A and 4B, are shown to a user in sequence. The first VPT Image 100 appears on screen for a short duration of time, then no image is shown for a short duration of time, and finally the second VPT Image is shown for a short duration of time. One of the two images will contain the "target", appearing in the target area the user is focusing on, that the user is expected to perceive. In the VPT of this example, the target appears in the second image, which is FIG. 4B.

After the images are shown, the user is asked to provide an input based upon his or her perception of the VPT Images 100 that were presented. For example, the user can be asked to indicate whether he or she perceived the target. The appropriate user input in this example then would be to acknowledge that the second image contained the target. The user can provide this input through a variety of mechanisms, for instance by answering a yes/no question, a multiple choice question, a true/false question, a right/left question, or other similar questions. The user provides the input using an input device such as a computer keyboard or mouse. Other input means, such as voice recognition, touch-screens, joysticks, trackballs, computer pens, or touch-pads can also be used. For some VPTs, such as those testing perception of contours, the input may not be a response to a question, but rather, the user may indicate a perceived contour formed by the images using a mouse to outline the contour.

Once the user inputs a response, the invention will generate one or more further VPTs to present to the user based at least in part upon the user's response to the preceding VPT. For example, if the user was unable to perceive the target in the preceding VPT, the further VPT can be made so that the target is easier to perceive for the user. Alternately, the further VPT can be designed to maintain the same level of difficulty, thereby taxing the user's visual perception process and further working the user at the thresholds of their visual perception abilities.

The further VPTs are generated by varying one or more parameters associated with the VPT Images 100. These parameters include but are not limited to contrast, spatial frequency, distance between images, local and global orientation, and the duration of time an image is displayed.

Figure 5:
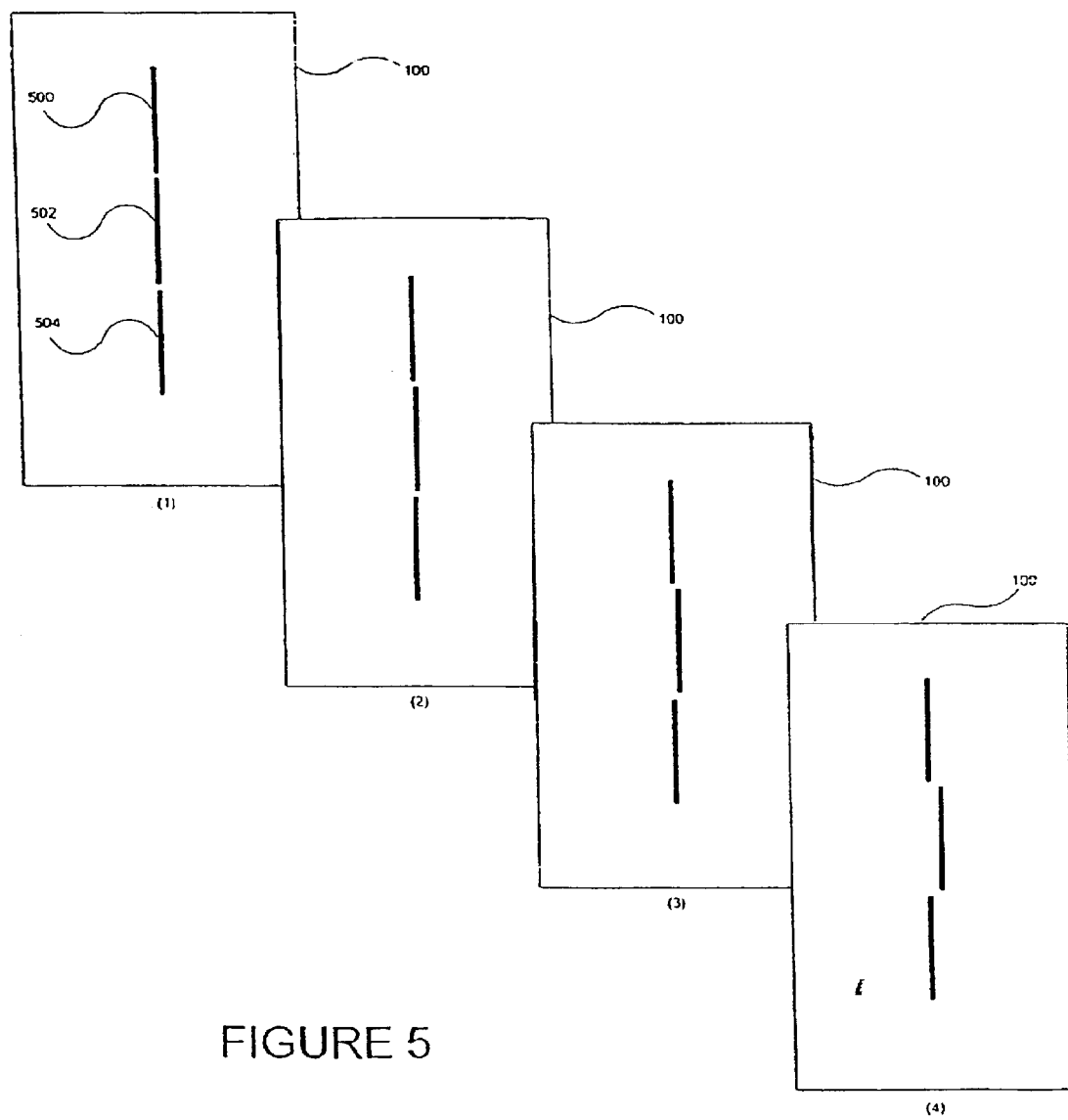
FIG. 5 illustrates another embodiment of a visual perception task.

Turning to FIG. 5, another example of a VPT is provided. This particular VPT is designed to evaluate the initial level of performance of a user in regard to the vernier acuity aspect of the visual perception process. Four steps are shown, corresponding to four different VPT Images that are presented to a user in sequence as described above. The first VPT Image 100 comprises three horizontal lines 500, 502, and 504 that are aligned vertically, as shown in step 1. In the subsequent VPT Images 100, steps 2 to 4, the middle vertical line 502 is gradually moved away from the top vertical line 500 and bottom vertical line 504 in a horizontal direction. At each step, the user provides inputs that indicate whether he or she can perceive that the middle vertical line 502 is offset from the top and bottom lines 500 and 504. When the user provides an input indicating that he or she detects the offset, the invention registers and stores this threshold level of vernier acuity. Again, it should be noted that this is just one of many possible embodiments of VPTs.

The administration of a series of VPTs designed to target a specific aspect of the visual perception process is referred to as a VPT Session. For example, a series of VPTs designed to improve a user's vernier acuity is referred to as a VPT Session for vernier acuity. Different VPT Sessions are designed to target all of the different aspects of the visual perception process, and the methods of the invention utilize all of these different VPT Sessions. Generally, only one aspect of a user's visual perception process is targeted for improvement at a time, accordingly, one VPT Session is typically administered at each sitting. However, depending on time constraints, a single VPT Session can be administered over the course of two or more sittings.

4. Communications Network Architecture

Figure 6:
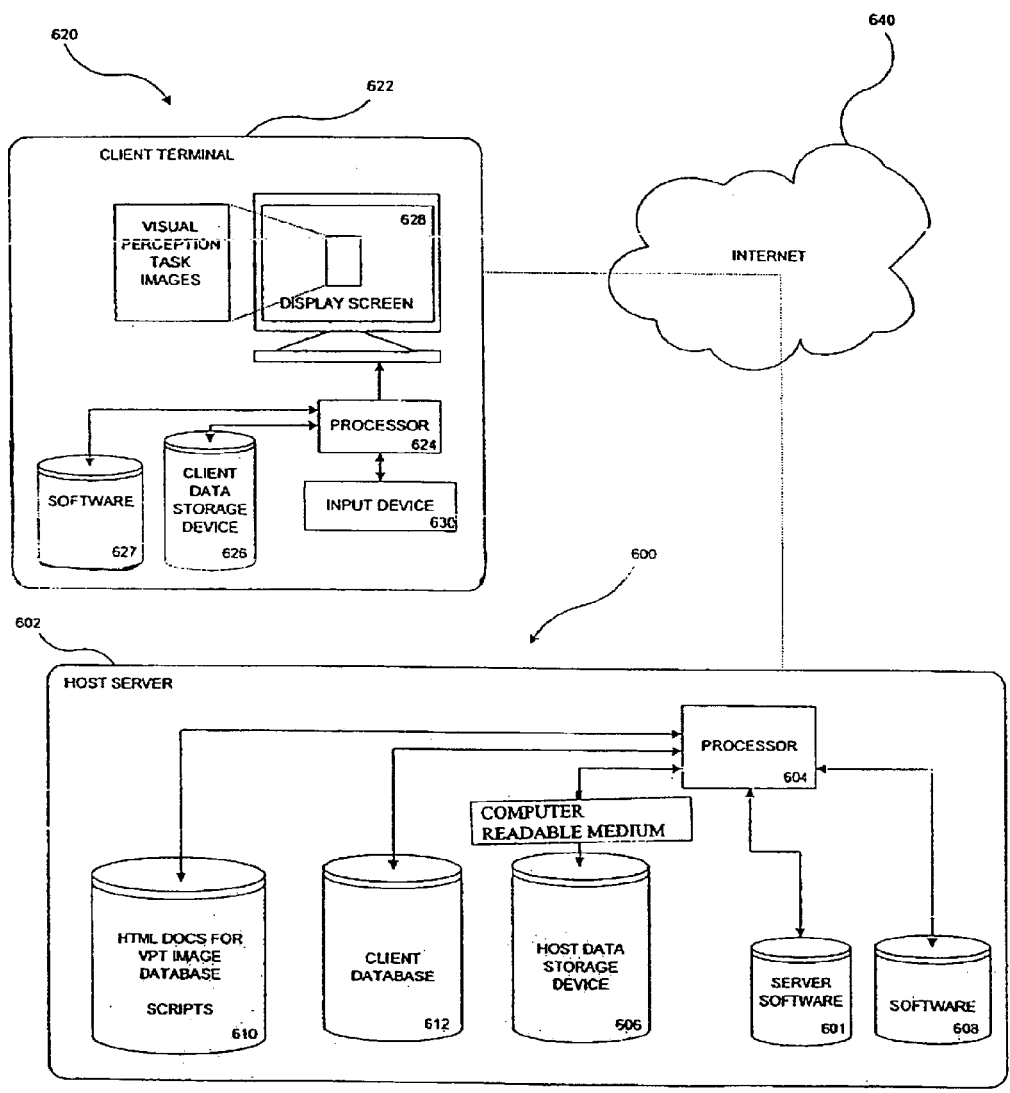
FIG. 6 illustrates an embodiment of an overall network configured to carry out the methods of the invention.

Turning to FIG. 6, a network architecture configured to carry out the methods of the invention is shown. The methods of the invention can be performed using a host server 600 and a client terminal 620. Host server 600 is a computer system 602 or device on a network with server software 601 configured to receive and answer requests for information. Typically, computer system 602 is also dedicated to storing data files and managing network resources, including network traffic. Computer system 602 or device generally includes a processor 604 and a data storage device 606, and is typically connected to a global communications network such as the Internet 640.

Host server 600, through processor 604, has access to software 608 comprising sequences of instructions that cause processor 604 to perform a number of acts in accordance with the methods described herein. In an alternative embodiment, host server 600 can also have access to a web page data storage device 610 that can store Hypertext Mark-Up Language (HTML) documents defining web pages for communicating with users, including HTML documents generated for the VPT Images 100. Web page data storage device 610 can also store computer program scripts to generate web pages using an Active Server Pages (ASP) specification or Common Gateway Interface (CGI) specification.

Host server 600 also has access to a client database 612 that stores information concerning users of the system. This information can include identification information and data relating to a user's performance during past VPT Sessions. In alternate embodiments, client database 612 may reside outside host server 600, such as at client terminal 620.

Client terminal 620 is a remote terminal that provides an interface for a user to access host server 600. Client terminal 620 is typically a computer system 622 or device that is communicatively coupled to host server 600 by a communications network, such as the Internet 640. Computer system 622 generally includes a processor 624, a data storage device 626, a display screen 628, an input device 630, and software 627 that comprises sequences of instructions that cause processor 624 to perform a number of acts in accordance with the methods described herein. An exemplary computer system for use in either the host server 600 or client terminal 620 is described below with reference to FIG. 10.

Figure 7:
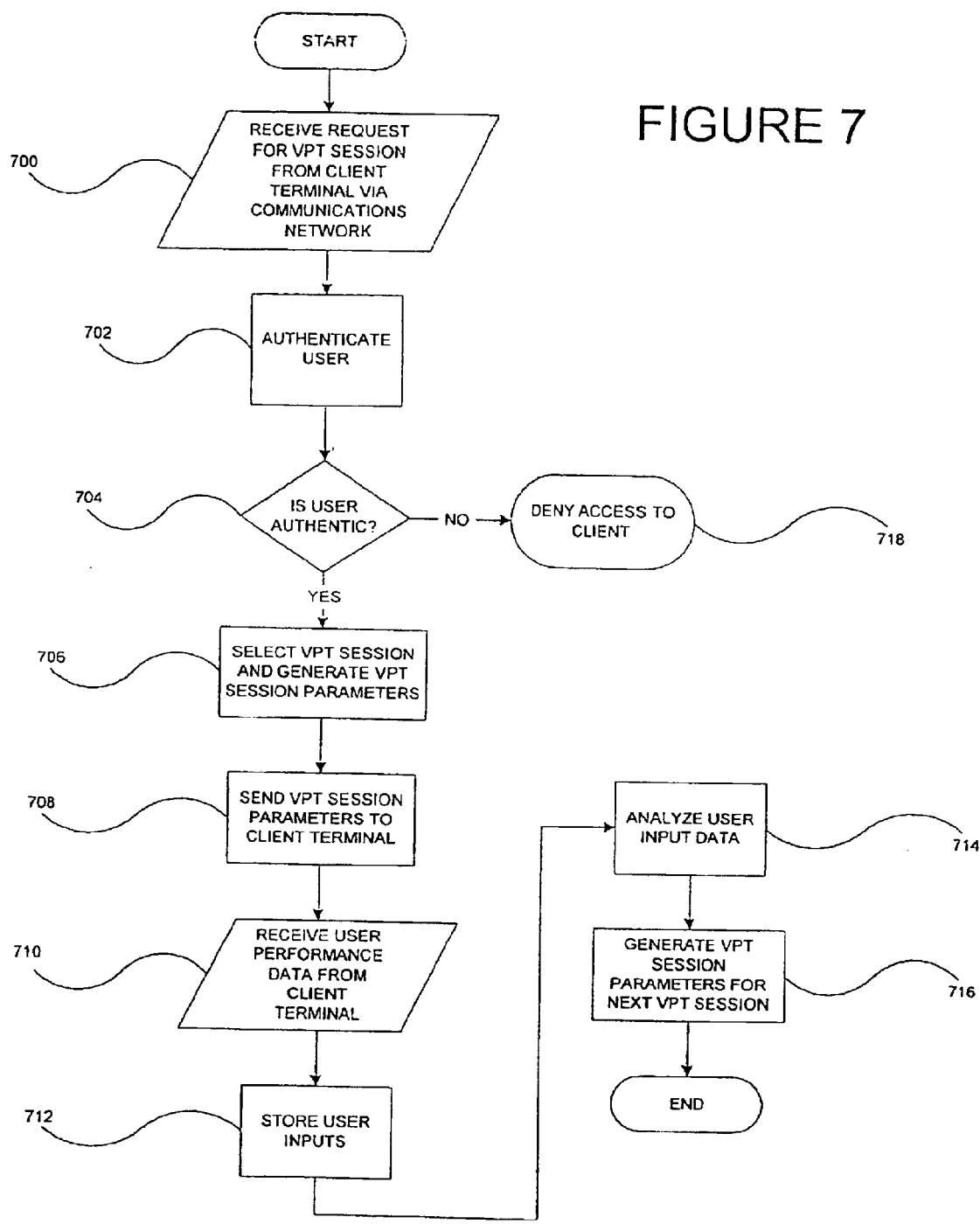
FIG. 7 is a flowchart depicting the methods of the invention from the perspective of the host server.

5. Methods for Administering Visual Perception Tasks Over a Communications Network Host Server-Side Methods Turning to FIG. 7, a flowchart depicting an embodiment of a method of the invention is shown. The flowchart illustrates how the method is carried out at host server 600. Starting with step 700, host server 600 first receives a request from client terminal 620 for access to a VPT Session. This request is sent from client terminal 620 to host server 600 over a communications network such as the Internet 640. For ease of reference, the Internet will be the communications network referenced. It should be noted, however, that any form of communications network may be utilized by the invention.

Host server 600 can make itself accessible for such a request from client terminal 620 by providing an Internet website. Users can visit the Internet website using a web browser such as Netscape Navigator (available at www.netscape.com) or Microsoft Internet Explorer (available at www.microsoft.com), or a specially developed web browser may be used to access the site. Users can then directly request access to a VPT Session from host server 600.

In step 702, an authentication routine is performed to determine whether the request from client terminal 620 is valid. In other words, host server 600 determines whether the user that is trying to access a VPT Session is authorized to do so. Generally, host server 600 does this by sending a request over the Internet to client terminal 620 for a username and password. The data then received from client terminal 620 in response to the username and password request is typically transmitted to host server 600 over the Internet in an encrypted format, or using certificates, which prevents unauthorized persons from viewing the data.

Moving to step 704, upon receiving the username and password data from client terminal 620, host server 600 compares that data to username and password data stored in client database 612. If host server 600 determines that the user is authentic, the process continues at step 706. If the user is deemed to be non-authentic, a message is sent to client terminal 620 informing the user that access to the VPT Sessions is denied, as shown in step 718. At that point, the user can be allowed to re-enter his or her username and password information a number of times. Generally, the number of times the user is permitted to re-enter the username/password information is limited to prevent users from trying to gain unauthorized access. After a predetermined number of failed authentication attempts, host server 600 will typically ignore further requests from client terminal 620 for a predetermined length of time.

In step 706, after host server 600 determines that the username and password supplied are genuine, a VPT Session is selected and an initial set of VPT Session parameters are generated. Typically, these parameters are defined in advance. The VPT Session, as well as the VPT Session parameters, are generated according to the methods described below with reference to FIG. 8. The VPT Session parameters define items such as contrast level, contours, spatial frequency, distance between objects, target placement, local and/or global orientations, and presentation time for each of the VPTs and VPT Images 100 being used to test or improve the visual perception process of a user. The process of generating further VPT Session parameters during administration of the methods of the invention is explained below with reference to step 716 of FIG. 7 and with reference to FIG. 8.

Moving to step 708, the initial VPT Session parameters are then delivered to client terminal 620 over the Internet 640. Software resident on client terminal 620 is configured to receive the VPT Session parameters and use them to dynamically generate VPT Images 100 and VPTs. The VPT Session parameters transmitted can be encrypted, or can use certificates, for security purposes so no person can intercept the data. Once the parameters are delivered, the VPT Session can be carried out solely at client terminal 620 without the need for further interaction with host server 600. This preferred configuration allows the VPT Session to be administered to the user without delay or interruption.

Alternatively, the VPT Session parameters can be sent as web pages in a format such as the Hyper-Text Markup Language (HTML) format. The web pages sent will generally be full screen pages, encompassing the entire viewable area of the display screen rather than appearing within a frame of a web browser.

In another alternative configuration, administration of the VPT Session can be carried out primarily by host server 600, thus requiring data to be transferred back and forth between host server 600 and client terminal 620 during the session itself.

Moving to step 710, after the VPT Session has been administered to the user, host server 600 receives a set of user performance data from client terminal 620. The user performance data is data relating to the user's performance, and can include some or all of the user inputs received by client terminal 620 during administration of the VPT Session. The user performance data is generated by client terminal 620, and then sent back to host server 600 over the Internet 640. This data can also be encrypted to prevent unauthorized persons from viewing the data.

In step 712, host server 600 stores the user performance data it receives from client terminal 620. The user performance data is generally stored on a data storage device, such as client database 612. The data may alternatively be stored on data storage device 606. This alternative may be preferred when, for instance, the personal information and medical records of clients are to be kept on a relatively secured storage device that is separate from the storage device that is storing the collection of user inputs. The data storage device 606 is further described below with reference to FIG. 10.

Moving to step 714, the host server 600 next analyzes the user performance data to unearth any visual perception deficiencies, and to determine the level of performance of the user's visual perception process. Software 608 provides instructions and data for processor 604 to carry out this analysis. A weighted average score can also be calculated for the user. This is typically done by comparing the user performance data to data collected from persons with normal vision (i.e. acceptable levels of performance for each of the different aspects of the visual perception process), which helps gauge the user's level of performance. Generally processor 604 performs such comparison, with data related to that of a normal observer typically being stored in data storage device 606.

Moving to step 716, the invention then generates new VPT Session parameters that can be used in the next VPT Session, based at least in part upon the user performance data that was received by host server 600, and based at least in part upon the analysis conducted upon the user performance data by processor 604. These new parameters again define specific VPT Images 100 and VPTs to further improve the user's visual perception ability based upon the user's level of performance. Host server 600 uses software 608 to make these analyses and determinations. Software 608 contains instructions regarding how to generate parameters for VPT Images 100 and VPTs that will further improve the visual perception of a user based on levels of performance during past VPT Sessions. Generally, these parameters are then stored until the user requests another VPT Session.

In an alternative embodiment of the invention, client terminal 620 downloads VPT Session parameters for a number of users at one time. For instance, client terminal 620 may be in communication with host server 600 for a period of time, for example in the morning, to download VPT Session parameters for a number of users. These users can be persons who have scheduled appointments to access client terminal 620 during that day. This eliminates the need for constant or frequent on-line communications, and can also eliminate the need for individual usernames and passwords for users as the entity running the client terminal can control who has access.

In this alternative, the sets of user performance data generated during the numerous VPT Sessions administered to all of the users can then be uploaded to host server 600 at one time. The data upload can take place anytime, for example during off peak hours, or even the next morning during the same period of time when new VPT Session parameters are being downloaded for that day's scheduled users. It should be noted that the period of time during which the uploading and downloading of data takes place can occur at any time of the day.

In another alternative embodiment, the VPT Images 100 are preformed and selected, rather than being generated dynamically. In such an embodiment, the VPT Session parameters comprise the specific VPT Images 100 themselves, rather than defining the images.

Selecting a VPT Session to Administer

Figure 8:
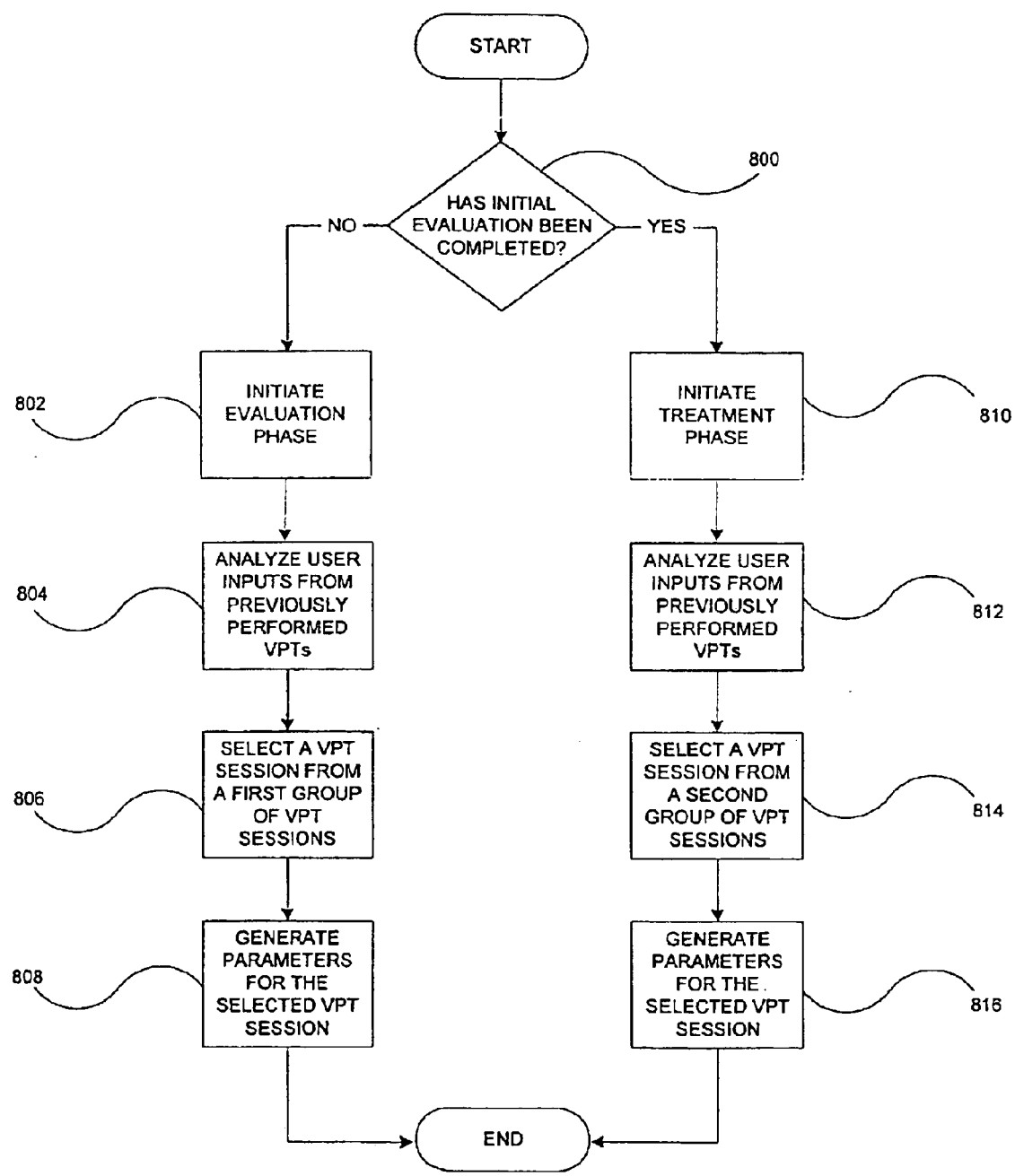
FIG. 8 is a flowchart depicting an embodiment of how the host server selects a visual perception task session for a user.

Turning to FIG. 8, a flowchart is illustrated that demonstrates how a VPT Session is selected. There are two forms of VPT Sessions available, an evaluation phase to ascertain a user's visual perception ability, and a treatment phase to improve the user's visual perception. Accordingly, as shown in step 800, the first step in selecting a VPT Session is to determine whether the user has undergone the evaluation phase. If an evaluation has not been completed, the next step in the process is to move on to step 802. Otherwise, the flowchart will continue at step 810.

Starting with the evaluation phase and step 802, a user undergoes the evaluation to enable the invention to ascertain the condition of the user's visual perception process. This data allows the invention to generate effective VPTs that target the user's visual perception deficiencies. It also allows the invention to have a baseline set of data to gauge whether the user's visual perception is improving over the course of a particular VPT Session and over time. The evaluation process can be performed as often as necessary or desired.

Moving to step 804, the invention analyzes any user inputs from past VPT Sessions. This data provides information that the invention can use in establishing parameters that select VPT Images 100 and VPT Sessions to use to evaluate the user's visual perception. For instance, if particular aspects of the user's visual perception have recently been evaluated, the invention can select a VPT Session that evaluates a different aspect. Or if the user inputs from past VPT Sessions show that the user is deficient in a particular aspect of their visual perception, the invention can select a VPT Session that further evaluates that aspect to determine whether there has been improvement or deterioration.

Moving to step 806, a VPT Session is selected from a first group of potential VPT Sessions. VPTs within each VPT Session are used to collect data from the user regarding different aspects of the user's visual perception process to detect the existence of any physical or neural defects. The invention uses VPTs to test for any one or all of the following:

reduced visual acuity,
abnormal contrast sensitivity functions,
reduced vernier acuity,
spatial distortion,
abnormal spatial interactions,
impaired contour detection,
abnormally high degrees of intrinsic noise,
as well as other aspects of the user's visual perception.

Moving to step 808, once the VPT Session has been selected, the invention generates parameters for the VPT Session. These parameters define the VPT Images 100 and VPTs that are to be presented to the user, and in particular control the difficulty of the VPTs as well as other characteristics. Again, data from past VPT Sessions, including VPT Session parameters generated in accordance with step 716 of FIG. 7 above, can be used in setting these parameters.

Moving to step 810 and the treatment phase of the invention, the invention can be used to improve various aspects of the visual perception process of a user and alleviate visual perception deficiencies. The flow of the treatment phase is almost identical to that of the evaluation phase.

Moving to step 812, user inputs from past VPT Sessions are analyzed. Next, as shown in step 814, a VPT Session is selected from a second group of VPT Sessions. This second group of VPT Sessions is different than the group described for the evaluation phase. Here, the second group of VPT Sessions comprises the following:
a lateral masking treatment VPT Session,
an acuity treatment VPT Session,
an elongated stimuli treatment VPT Session,
a stereoscopic treatment VPT Session,
and other treatment VPT Sessions.

Moving to step 816, as was the case for the evaluation phase, once a VPT Session has been selected the invention generates parameters that again define the VPT Images 100 and VPTs that are to be presented to the user. Data from past VPT Sessions can be used in generating these parameters, including VPT Session parameters generated in accordance with step 716 of FIG. 7 above.

Client Terminal-Side Methods

Figure 9:
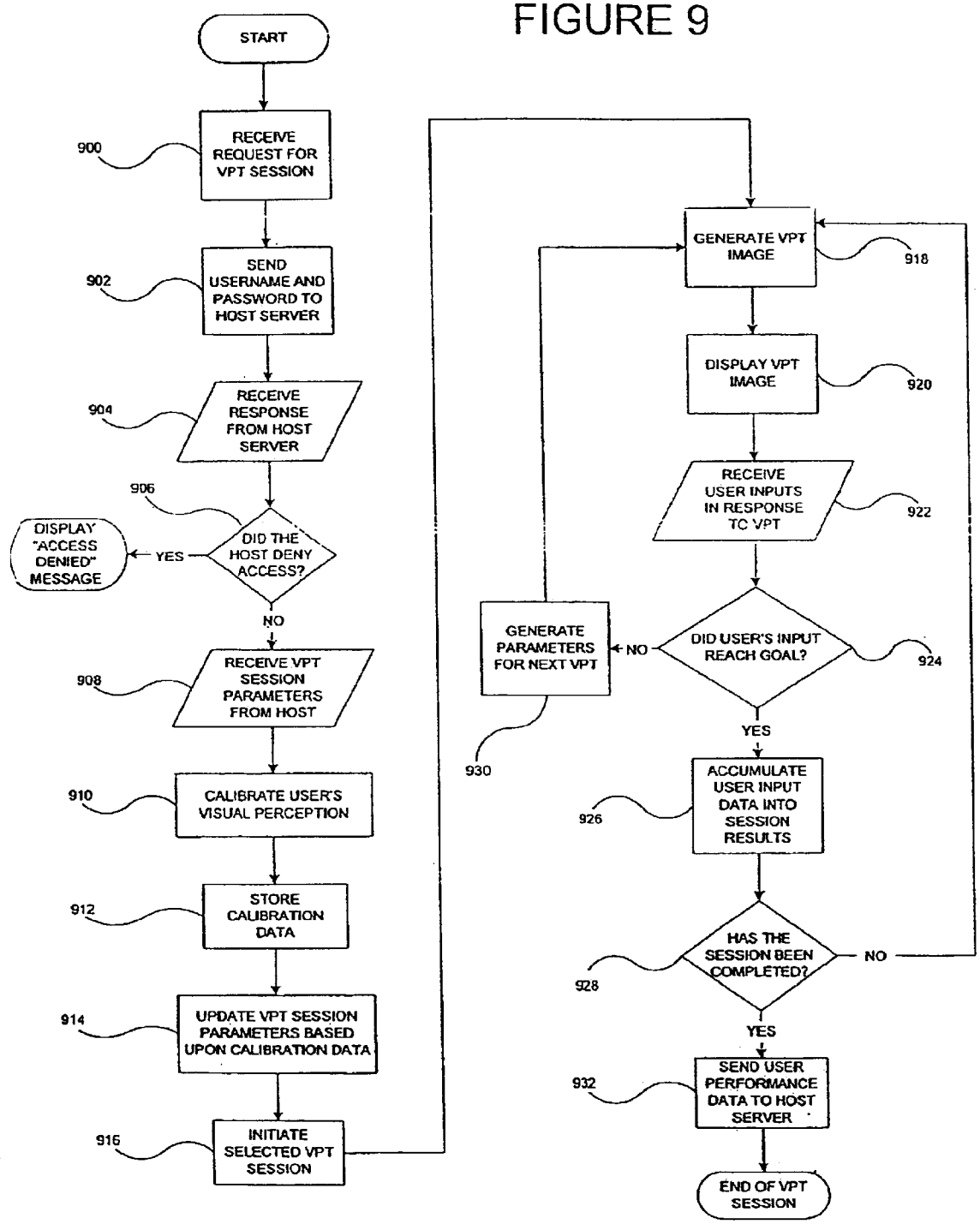
FIG. 9 is a flowchart depicting the methods of the invention from the perspective of the client terminal.

FIG. 9 is a flowchart illustrating how the methods of the invention are carried out at client terminal 620. Starting with step 900, client terminal 620 receives a request for a VPT Session from a user. For example, a user can arrive at client terminal 620 and enter a request for a VPT Session using an input device, such as a keyboard, at client terminal 620. The process of requesting a VPT Session generally comprises visiting a web site, such as a home page or authentication page provided by host server 600, and entering a username and password. The software that requests the username and password may be located on either host server 600 or client terminal 620.

Moving to step 902, the VPT Session request and username/password information is sent from client terminal 620 to host server 600 over a communications network such as the Internet 640. Again, the Internet will be used herein as the communications network. This transmission of data can be encrypted or use certificates to prevent others from accessing the username and password information.

In step 904, client terminal 620 receives a response from host server 600 that either allows or denies access to a VPT Session. The response is transmitted over the Internet 640 and is sent after host server 600 has determined if the username and password supplied are authentic. As shown in step 906, if the user is authentic and access is granted, the process continues at step 908. Alternately, if host server 600 determines that the user is not authentic, access to a VPT Session is denied and the process ends with a message to the user indicating the denial of access.

Moving now to step 908, VPT Session parameters for the current VPT Session are delivered to client terminal 620 from host server 600. These VPT Session parameters are used to define the VPTS, and VPT Images 100, that are presented to the user. The process of generating the VPT Session parameters was explained above with reference to steps 706 and 716 of FIG. 7, and steps 808 and 816 of FIG. 8.

Client terminal 620 has software residing on it configured to administer VPT Sessions to a user, and generally only requires VPT Session parameters from host server 600 to deliver the VPT Session. The software can be sent to client terminal 620 in any of a number of ways, including by Internet download, or via installation off of a magnetic or optical disk.

In step 910, the invention calibrates the user's visual perception. The visual perception ability of a user can vary from day to day based on a variety of factors such as stress, energy level, fatigue, previous meals, time spent in front of a computer screen or television, and many others. Therefore the invention will run one or more tests of the user's visual perception to see if their visual perception ability is diminished due to these types of factors.

Moving to steps 912 and 914, the invention stores the collected calibration data and updates the VPT Session parameters downloaded during step 908. The parameters are updated to compensate for any diminished visual perception ability detected during the calibration step 910, thereby making the current VPT Session more effective and efficient.

Moving to step 916, the VPT Session is started. The VPT Session selected during the selection phase described in FIG. 8 is used.

In step 918, the invention generates one or more VPT Images 100 using the VPT Session parameters. Again, the parameters provided by host server 600 will be used to generate the VPT Images 100 on the fly. In another embodiment, the invention may use preformed VPT Images 100 and simply select which VPT Image 100 to use.

Moving to step 920, after the one or more VPT Images 100 have been generated, they are displayed on a display screen. If there are two or more VPT images 100, they are generally displayed sequentially, typically with a pause between each of the VPT Images 100. For example and as explained above, if there are two VPT Images 100, generally the first VPT Image 100 is displayed for a duration of time, then a duration of time passes where no image is shown, and then the second VPT Image 100 is shown for a duration of time. This routine for displaying VPT Images 100 constitutes one type of Visual Perception Task. Other forms of VPTs are also possible.

During the VPT a target is shown in at least one of the VPT Images 100. Then, as shown in step 922, the invention receives an input from the user indicating whether or not the user correctly perceived the target. This input from the user is important because the invention uses the user inputs to gauge a user's visual perception ability and to analyze the user's performance over one or more VPT Sessions. The invention also uses the user inputs to adjust the VPT Session parameters used in subsequent VPT Images 100.

Moving to step 924, the invention determines whether the user input demonstrates that the user has reached a predefined goal. This goal is set by the invention based on a variety of factors, including how the user has performed in previous VPT Sessions and during evaluation phases. An example of a goal can be to administer VPTs to the user until a desired level of improvement has been achieved.

Moving to step 930, if the goal has not been met, the invention generates new VPT Images 100 that are used in a subsequent VPT, again based on the VPT Session parameters (which can be modified as the VPT Session is administered). The new VPT Images 100 are generally variations of the previous VPT Images 100, wherein parameters such as contrast, distance between objects, color, shape, size, or other parameters are changed. The new parameters can vary the difficulty level of the VPT that is displayed, generally based at least in part upon the user's inputs and performance over the preceding one or more VPTs.

For instance, if the user is having a difficult time perceiving a target, the new parameters can make the next VPT less difficult and closer to the user's threshold. The user's threshold level generally corresponds to a point where the user is first able to successfully complete a given VPT. In addition, incorrect responses may also trigger a buzzer or some other auditory or visual signal. And if the user is consistently perceiving the target correctly, the new parameters can make the next VPT more difficult. The same VPT may be presented to a user a number of times before moving on to the next VPT, to more accurately gauge the user's performance for a given VPT. Once the new parameters are chosen, the invention moves back to step 918 and displays the next set of VPT Images 100.

Moving to step 926, after the goal has been reached, the invention accumulates the inputs into the VPT Session results and generated the user performance data. These results can later be analyzed by the invention to ascertain the condition of the user's visual perception process, and determine whether it is improving or regressing.

Moving to step 928, the invention determines whether the entire VPT Session has been completed. If so, the user performance data, including the accumulated user inputs, are sent to host server 600 over the Internet 640 as shown in step 932, and this particular VPT Session is ended. The user performance data can be sent to host server 600 in an encrypted format, or using certificates, to prevent unauthorized persons from viewing the user input data. If the VPT Session has not been completed, the invention moves back to step 918 and new VPT Images 100 are generated to continue the current VPT Session.

6. Hardware Overview

Figure 10:
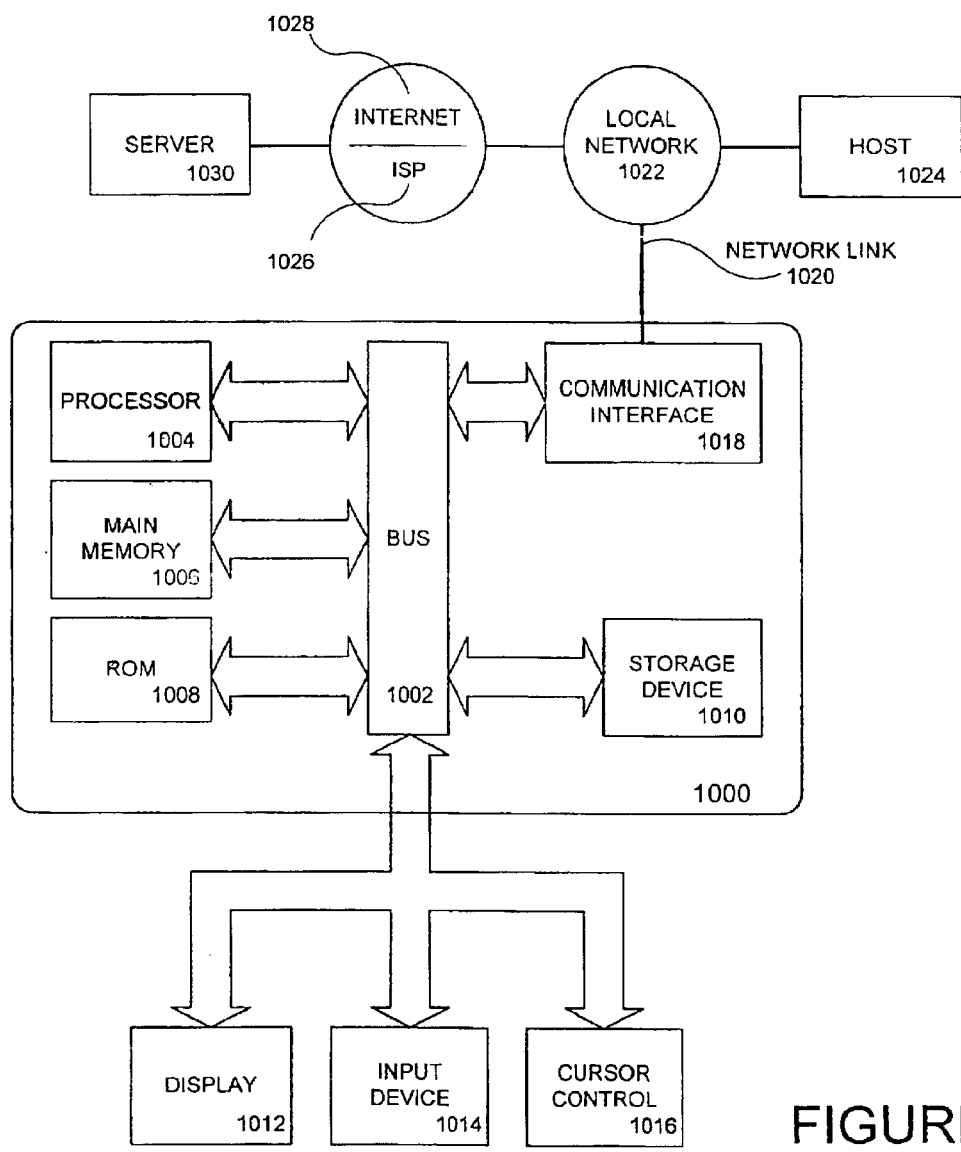
FIG. 10 illustrates an embodiment of an apparatus configured to carry out the methods of the invention.

FIG. 10 is a block diagram of an exemplary computer system 1000 upon which methods of the invention can be implemented. The computer system of FIG. 10 can be used for host server 600, and/or for client terminal 620.

Computer system 1000 includes a bus 1002, or other communication mechanism for communicating information, and a processor 1004 coupled with bus 1002 for processing information. Computer system 1000 also includes a main memory 1006, such as a random access memory ("RAM"), or other dynamic (or "volatile") storage device, coupled to bus 1002. The main memory 1006 stores information and instructions executed by processor 1004 during execution. Main memory 1006 also stores temporary variables or other intermediate information during execution of instructions by processor 1006.

Computer system 1000 further includes a read only memory ("ROM") 1008 or other static (or "persistent") storage device (e.g., FLASH, PROM, EEPROM, etc.) coupled to bus 1002. The ROM 1008 stores static information and instructions for processor 1004. It is worth noting that one or more banks of memory can comprise ROM 1008. A storage device 1010, such as a magnetic disk or optical disk (or "hard disk", or "hard drive"), or another form of persistent storage device, is coupled to bus 1002. The storage device 1010 uses a computer readable medium to store information such as data structures and instructions, for example, accumulated user input data from completed VPT Sessions, processor executable instructions (i.e. software) configured to carry out the methods described above with reference to host server 600 and client terminal 620, and/or structures relating to the operating system or application programs that use the operating system.

Computer system 1000 is preferably coupled via bus 1002 to a display device 1012, such as a cathode ray tube ("CRT") or an active or passive-matrix display. The display 1012 presents images to an end-user, such as VPT Images 100. An input device 1014, including alphanumeric and other keys, is coupled to bus 1002. The input device 1014 communicates information and command selections to processor 1004. Another type of user input device is cursor control 1016, such as a mouse, trackball, or cursor direction keys, for communicating direction information and command selections to processor 1004 and for controlling cursor movement on display 1012. This input device 1014 typically has two degrees of freedom in two axes, a first axis (e.g., x) and a second axis (e.g., y), that allows the device to specify positions in a plane.

According to an aspect of the invention, the processor 1004 in the computer system 1000 executes one or more sequences of instructions (i.e. software 1005), contained in main memory 1006. Such instructions are read into main memory 1006 from another computer-readable medium, such as storage device 1010 or ROM 1008. The instructions can be executable object code or interpreted code that is processed by a run-time engine (e.g., Javascript).

Execution of the sequences of instructions contained in main memory 1006 causes processor 1004 to perform the methods of the invention as described herein, such as the methods described with reference to host server 600 and/or client terminal 620 above. In alternative embodiments, hardwired circuitry can be used in place of or in combination with software instructions to implement the invention. Thus, embodiments of the invention are not limited to any specific combination of hardware circuitry and software.

The term "computer-readable medium" as used herein refers to any medium that participates in providing instructions to processor 1004 for execution. Such a medium can take many forms, including but not limited to, non-volatile media, volatile media, and transmission media. Non-volatile media includes, for example, optical or magnetic disks, such as storage device 1010. Volatile media includes dynamic memory, such as main memory 1006.

Transmission media includes coaxial cables, copper wire and fiber optics, including the wires that comprise bus 1002. Transmission media can also take the form of acoustic or light waves, such as those generated during radio-wave and infrared data communications.

Common forms of computer-readable media include, a floppy disk, a flexible disk, a hard disk, a magnetic tape, or any other magnetic media, a CD-ROM, any other optical media, punchcards, a paper-tape, any other physical media with patterns of holes, a RAM, a ROM, a FLASH, or any other memory chip or cartridge, a carrier wave as described hereinafter, or any other media from which a computer can read.

Various forms of computer-readable media can be involved in carrying one or more sequences of one or more instructions to processor 1004 for execution. For example, the instructions can initially be carried on a magnetic disk of a remote computer. The remote computer can load the instructions into its dynamic memory and send the instructions over a telephone line using a modem. A modem local to computer system 1000 can receive the data on the telephone line and use an infrared transmitter to convert the data to an infrared signal. An infrared detector coupled to bus 1002 can receive the data carried in the infrared signal and place the data on bus 1002. Bus 1002 carries the data to main memory 1006, from which processor 1004 retrieves and executes the instructions. The instructions received by main memory 1006 can optionally be stored on storage device 1010 before or after execution by processor 1004.

Computer system 1000 also includes a communication interface 1018 coupled to bus 1002. Communication interface 1018 provides a two-way data communication coupling to a network link 1020 that is connected to a local network 1022. For example, communication interface 1018 can be an integrated services digital network ("ISDN") card or a modem to provide a data communication connection to a corresponding type of telephone line. As another example, communication interface 1018 can be a local area network ("LAN") card to provide a data communication connection to a compatible LAN. Wireless links can also be implemented. In any such implementation, communication interface 1018 sends and receives electrical, electromagnetic or optical signals that carry digital data streams representing various types of information.

Network link 1020 preferable provides data communication through one or more networks to other data devices. For example, network link 1020 can provide a connection through local network 1022 to a host computer 1024 or to data equipment operated by an Internet Service Provider ("ISP") 1026. ISP 1026 in turn provides data communication services through the Internet 1028. Local network 1022 and Internet 1028 both use electrical, electromagnetic or optical signals that carry digital data streams. The signals through the various networks and the signals on network link 1020 and through communication interface 1018, which carry the digital data to and from computer system 1000, are exemplary forms of carrier waves transporting the information.

Computer system 1000 can send messages and receive data, including program code, through the network(s), network link 1020 and communication interface 1018. In the Internet example, a server 1030 might transmit requested code for an application program through Internet 1028, ISP 1026, local network 1022 and communication interface 1018—for example using the FTP protocol. In accordance with the invention, one such downloaded application is executable software code or computer configuration parameters that perform the methods of the invention.

The received code can be executed by processor 1004 as it is received, and/or stored in main memory 1006, storage device 1010, or other non-volatile storage for later execution. In this manner, computer system 1000 can obtain application code in the form of a carrier wave.

Thus, methods and systems for analyzing and improving the visual perception process of a person have been disclosed. It should be noted that the disclosed methods and systems are useful for improving the visual perception of any person, no matter whether the person has normal or abnormal visual perception. The invention can also be used to improve vision of observers suffering from problems such as amblyopia or dyslexia. Even persons with anatomical or functional problems, such as macular degeneration, can improve what vision they have with the methods and apparatus of the invention.

While various embodiments of the invention have been shown and described, it will be apparent to those skilled in the art that numerous alterations may be made without departing from the inventive concepts presented herein. Thus, the invention is not to be limited except in accordance with the following claims and their equivalents.

What is claimed is:

1. A system for improving the visual perception ability of a user, comprising:
   a client terminal including a display device, an input device, and a client processor;
   and a host server including a host storage device, and a host processor communicatively coupled to said client processor;
   said host storage device having stored therein a first plurality of parameters of images selectable to test the visual perception ability of the person with respect to at least one visual defect and to elicit responses from the person indicative of the presence or absence of said at least one visual defect, and a second plurality of parameters of images designed to treat the person with respect to a detected visual defect and thereby to improve the visual perception ability of the person with respect to such detected visual defect;
   said display device being controlled by said client processor and host processor for displaying to the person, selected images of said first plurality of parameters and of said second plurality of parameters;
   said client processor and host processor being controlled by said client input device:
      (a) to receive said first plurality of parameters, to generate a first plurality of images corresponding thereto, and to display said first plurality of images in said display device;
      (b) to register responses inputted by the user via said input device;
      (c) to utilize said user responses to select the parameters of said second plurality of images in said host storage device corresponding to the images designed to treat the person with respect to a visual defect detected from said responses; and
      (d) to control said display device to display to the user, in a treatment phase, the selected images in said second plurality in at least one treatment session until the visual perception ability of the person has been improved with respect to said detected visual defect.

2. The system of claim 1, wherein the client terminal and the host server are communicatively coupled via a communications network.

3. The system of claim 2, wherein the communications network comprises the Internet.

4. The system of claim 1, wherein the client terminal further comprises:
   a client storage device comprising a computer-readable medium communicatively coupled to the client processor;
   a persistent memory communicatively coupled to the client processor,
   and a communication interface communicatively coupled to the client processor, said interface being configured to transmit data to and from the host server via the communications network.

5. The system of claim 4, wherein one or more sequences of client processor executable instructions are stored in the client storage device which cause the client processor to perform a number of acts, comprising:
   generating an image;
   receiving an input from a user based on the user's perception of the image; and
   generating a further image based on the input.

6. The system of claim 5, wherein the act of generating a further image is carried out by modifying one or more parameters of the image.

7. The system of claim 5, wherein the act of generating a further image is carried out by selecting a new image from a predefined set of images.

8. The system of claim 5, wherein the act of generating a further image is carried out using a configuration that is more difficult to perceive if the user does accurately perceive a characteristic of the image.

9. The system of claim 5, wherein the act of generating a further image is carried out using a configuration that is less difficult to perceive if the user does not accurately perceive a characteristic of the image.

10. The system of claim 5, wherein the acts to be performed by the client processor further comprise generating a series of images used to ascertain the visual and neurological perception ability of the user.

11. The system of claim 5, wherein the image generated comprises one or more Gabor patches.

12. The system of claim 1, wherein the host server further comprises:
- a persistent memory communicatively coupled to the host processor, and
- a communication interface communicatively coupled to the host processor, said interface being configured to transmit data to and from the client terminal via the communications network.

13. The system of claim 12, wherein the host server further comprises:
- a user database communicatively coupled to the processor for storing user information.

14. The system of claim 12, wherein one or more sequences of host processor executable instructions are stored in the host storage device which cause the host processor to perform a number of acts, comprising:
- selecting parameters and delivering them to the client terminal;
- receiving a set of user inputs from the client terminal;
- analyzing the set of user inputs; and
- generating one or more farther parameters to deliver to the client terminal based at least in part upon the analysis performed on the set of user inputs.

15. The system of claim 14, wherein the acts performed by the one or more sequences of host processor executable instructions further comprise authenticating a user.

16. A method of improving the visual perception ability of a person, comprising:
- in a client terminal, displaying to the person, in at least one evaluation session of an evaluation phase, a plurality of images selected to test the visual perception ability of the person with respect to at least one visual defect, and to elicit responses from the person indicative of the level of the person's visual perception ability with respect to said at least one visual defect;
- communicating the responses of the person to a remotely-located host server;
- utilizing said responses to select in the host server another plurality of images designed to treat the person with respect to a detected visual defect and thereby to improve the visual perception ability of the person with respect to the detected visual defect;
- and in the client terminal, displaying to the person, in a treatment phase, said another plurality of images in at least one treatment session until the visual perception ability of the person has been improved with respect to said detected visual defect.

17. The method according to claim 16, wherein said treatment phase includes a plurality of treatment sessions in each of which are displayed to the person a plurality of images designed to elicit responses to be used for selecting the plurality of images in the subsequent treatment session such as to progressively improve the visual perception ability of the person with respect to such detected visual defect.

18. The method according to claim 17, wherein at least one predetermined parameter of the plurality of images displayed in one treatment session is varied in the subsequent treatment session.

19. The method according to claim 17, wherein each of said treatment sessions includes a plurality of visual perception tasks in each of which there is displayed to the person at least one image designed to elicit a response useful for selecting at least one other image to be displayed in the subsequent visual perception task of the respective treatment session such as to progressively improve the visual perception ability of the person with respect to the detected defect.

20. The method according to claim 16, wherein said evaluation phase includes a plurality of evaluation sessions in each of which at least one plurality of images are displayed to the person to elicit responses, the responses of each evaluation session being utilized to select the plurality of images to be displayed in the next evaluation session.

21. The method according to claim 20, wherein each of said evaluation sessions includes a plurality of visual perception tasks in each of which there is displayed to the person at least one image designed to elicit a response useful for selecting at least one other image to be displayed in the subsequent visual perception task of the respective evaluation session such as to progressively improve the evaluation of the visual perception ability of the person with respect to the detected defect.

22. The method according to claim 16, wherein said plurality of images in at least the treatment phase are images based on Gabor Functions.

* * * * *